United States Patent [19]

Moenning

[11] Patent Number: 5,766,220

[45] Date of Patent: Jun. 16, 1998

[54] APPARATUS AND METHOD FOR PROTECTING A PORT SITE OPENING IN THE WALL OF A BODY CAVITY

[76] Inventor: Stephen P. Moenning, 124 Hibiscus, Punta Gorda, Fla. 33950

[21] Appl. No.: 608,644

[22] Filed: Feb. 29, 1996

[51] Int. Cl.$^6$ ................................................. A61B 17/08
[52] U.S. Cl. ........................ 606/213; 606/215; 606/191; 606/192; 604/164; 604/171; 604/174
[58] Field of Search ........................... 606/213, 214, 606/215, 191, 192, 193, 197; 604/164, 165, 171, 268, 174, 104, 105

[56] References Cited

U.S. PATENT DOCUMENTS

| | | | |
|---|---|---|---|
| 4,535,773 | 8/1985 | Yoon | 604/51 |
| 4,601,710 | 7/1986 | Moll | 604/165 |
| 4,931,042 | 6/1990 | Holmes et al. | 604/164 |
| 5,066,288 | 11/1991 | Deniega et al. | 604/274 |
| 5,114,407 | 5/1992 | Burbank | 604/164 |
| 5,147,316 | 9/1992 | Castillenti | 604/164 |
| 5,152,754 | 10/1992 | Plyley et al. | 604/164 |
| 5,290,249 | 3/1994 | Foster et al. | 604/174 |
| 5,318,580 | 6/1994 | Greal | 606/185 |
| 5,338,305 | 8/1994 | Plyley et al. | 604/164 |
| 5,342,382 | 8/1994 | Brinkerhoff et al. | 606/184 |
| 5,350,393 | 9/1994 | Yoon | 606/185 |
| 5,366,446 | 11/1994 | Tal et al. | 604/110 |
| 5,368,545 | 11/1994 | Schaller et al. | 600/37 |
| 5,370,647 | 12/1994 | Graber et al. | 606/127 |
| 5,391,156 | 2/1995 | Hildwein et al. | 604/174 |

FOREIGN PATENT DOCUMENTS

| | | |
|---|---|---|
| 0 542428 A | 5/1993 | European Pat. Off. . |
| WO 95/24864 | 9/1995 | WIPO . |

OTHER PUBLICATIONS

Bernstein, Mitchell et al., "Laparoscopic Resection for Colorectal Cancer: A USA Perspective", Seminars in Laparoscopic Surgery, vol. 2, No. 4 (Dec.), 1995: pp. 216–223.

Easter, David W., "Potential for Abdominal Wall Implantation After Laparoscopic Procedures of the Hepatobiliary Tract", Seminars in Laparoscopic Survey, vol. 2, No. 3, (Sep.), 1995: pp. 163–166.

Greene, Frederick, "Preface", Seminars in Laparoscopic Surgery, vol. 2, No. 3 (Sep.) 1995; pp. 153–154.

Greene, Frederick, "Principles of Cancer Biology in Relation to Minimal Access Surgical Techniques", Seminars in Laparoscopic Surgery, vol. 2, No. 3 (Sep.) 1995 pp. 155–157.

Hartley, J.E. et al., "Laparoscopic Resection for Colorectal Cancer: A European Perspective", Seminars in Laparoscopic Surgery, vol. 2, No. 4 (Dec.) 1995: pp. 224–234.

(List continued on next page.)

*Primary Examiner*—Michael Buiz
*Assistant Examiner*—Tina T. D. Pham
*Attorney, Agent, or Firm*—Maginot, Addison & Moore

[57] ABSTRACT

A medical apparatus includes a trocar assembly including a cannula and a trocar. The medical apparatus further includes a sleeve having a number of sealing members extending therefrom, and a passageway extending therethrough, with the trocar assembly being positioned within the passageway of the sleeve. The sleeve is positionable within an opening defined in a wall of a body cavity. Moreover, the sealing members are movable between (1) a first orientation in which the sealing members are positioned to facilitate advancement of the sleeve into the opening, and (2) a second orientation in which the sealing members are positioned to prevent fluid communication between an area inside of the body cavity and an area outside of the body cavity through a space defined between the opening of the body cavity and the sleeve. A medical procedure which uses the medical apparatus is also disclosed.

8 Claims, 7 Drawing Sheets

OTHER PUBLICATIONS

Heald, R.J., "Laparoscopic Resection for Colorectal Cancer: Limitations and Concerns", Seminars in Laparoscopic Surgery, vol. 2, No. 4, (Dec.) 1995: pp. 242–245.

Liberman, M.A., et al., "Laparoscopic Colectomy vs Traditional Colectomy for Diverticulitis Outcome and costs", Surg Endosc (1996) 10:15–18.

Lord, S. Alan, et al. "Laparoscopic Resections for Colorectal Carcinoma A Three Year Experience", Dis Colon Rectum vol. 39 No. 2: pp. 148–153 (Feb. 1996).

Sailer, M., et al., "Peritoneal Seeding of Gallbladder Cancer After Laparoscopic Cholecystectomy", Surg Endosc (1995) 9: 1298–1300.

Melzer, Andreas, et al., "Ports, Trocars/Cannulae, and Access Techniques", Seminars in Laparoscopic Surgery, vol. 2, No. 3 (Sep.), 1995: pp.179–204.

Mouiel, Jean, et al., "Port–Site Recurrence of Cancer Associated With Laparoscopic Diagnosis and Resection: The European Experience" Seminars in Laparoscopic Surgery, vol. 2, No. 3 (Sep.), 1995 pp. 167–175.

Savalgi, Raghu S. "Mechanism of Abdominal Wall Recurrence After Laparoscopic Resection of Colonic Cancers", Seminars in Laparoscopic Surgery, vol. 2, No. 3 (Sep.), 1995 pp. 158–162.

Stitz, Russell W., "Laparoscopic Resection for Colorectal Cancer: An Australian Perspective" Seminars in Laparoscopic Surgery, vol. 2, No. 4 (Dec.), 1995: pp. 235–241.

Treat, Michael R., "Mechanisms to Reduce Incidence of Tumor Implantation During Minimal Access Procedures for Colon Cancer" Seminars in Laparoscopic Surgery, vol. 2, No. 3 (Sep.), 1995: pp. 176–178.

APPARATUS AND METHOD FOR PROTECTING A PORT SITE OPENING IN THE WALL OF A BODY CAVITY

BACKGROUND OF THE INVENTION

The present invention generally relates to an apparatus and method for protecting a port site opening in the wall of a body cavity. The present invention particularly relates to an apparatus and method for protecting a port site opening in the wall of a body cavity which is used with a trocar assembly.

Minimally invasive surgical techniques, such as laparoscopic surgery, typically include using a trocar to create a small hole or port in a wall of a body cavity so as to gain access to the body cavity. Surgery performed by using these techniques is generally associated with lower postoperative morbidity, shorter postoperative stay, less postoperative pain, decreased cost, and quicker recovery as compared to "open" or conventional surgical techniques. Because of the aforementioned advantages, these minimally invasive techniques are being applied to an increasing variety of all surgical procedures. For example, laparoscopic procedures for the resection of malignancies have emerged. In particular, laparoscopic colectomy for carcinoma of the colon has been developed, and it has been reported that the initial results of these procedures have advantages over operations performed in the traditional open manner. Moreover, it is hoped that the long term results of these procedures will be comparable, or better than, those performed in the traditional open manner.

However, the field of laparoscopic surgery for cancer has been delayed in its development because of the major concern regarding the implantation of tumor cells in the port site wound. Minimally invasive surgical techniques for treating cancer require the removal of a malignant neoplasm through the small incision or port site created by a trocar. These procedures require the dragging of tumor tissue through the port site which creates a risk of implanting tumor cells in the walls of the wound forming the extraction site. An additional concern is that tumor cells exfoliated during the procedure will come into contact with, and contaminate, the port site wound. This contamination can occur as a result of the exfoliated tumor cells being in fluid communication with the port site wound. Regardless of how these cells contaminate the wound, once implanted therein, viable tumor cells can cause a subcutaneous metastases or "port/extraction site recurrence" after the resection of malignant tissue. In fact, numerous port site recurrences have been documented in the medical literature heretofore; and subcutaneous metastases after laparoscopic resection of malignant tissue has been described as a potentially serious complication of laparoscopic cancer surgery. These "port/extraction site recurrences" have delayed the advancement of laparoscopic cancer surgery.

Furthermore, laparoscopic surgery performed for general surgery, gynecological surgery, urological surgery, or any other intra-abdominal infection is associated with a small but real incidence of port site wound infection. The infecting bacteria causing these illnesses can contaminate the port site wound by the same mechanism as discussed above with reference to tumor cell contamination, and these infections can increase a patients morbidity and consequently the length of a patient's hospital stay, thereby considerably increasing their hospital bill.

Therefore, in light of the above discussion, it is apparent that an apparatus for preventing port site tumor implantation and reducing the incidence of port site infection, is desirable. The present invention provides such an apparatus in the form of a protective trocar sleeve. One advantage the present invention has over the prior art is that it can be retrofit to existing trocar assembly technology. Moreover, once attached, the described invention adds only a minimal amount of bulk to the diameter of the trocar assembly.

In use, the present invention protects the port site from infection or tumor cell implantation thereby lowering the morbidity and mortality of a wide variety of minimally invasive surgical techniques. The present invention allows the field of laparoscopic surgery to be safely applied to all forms of cancer surgery while minimizing "port site recurrences." The present invention also allows the field of laparoscopic surgery to be safely applied to all forms of laparoscopy while minimizing port site infections.

SUMMARY OF THE INVENTION

In accordance with one embodiment of the present invention, there is provided a medical apparatus which includes a trocar assembly having a cannula and a trocar. The medical apparatus also includes a sleeve having a number of sealing members, and a passageway extending therethrough, with the trocar assembly positioned within the passageway of the sleeve.

Pursuant to another embodiment of the present invention, there is provided a medical apparatus, including a sleeve having a number of sealing members attached and a passageway extending therethrough. The medical apparatus also includes a cannula positioned within the passageway of the sleeve, with the cannula defining a lumen through which medical instruments may be advanced.

According to yet another embodiment of the present invention, there is provided an apparatus for use with a trocar assembly. The apparatus includes a sleeve having a number of sealing members, and a passageway extending therethrough, the sealing members being movable between (1) a first orientation in which the sealing members are positioned to facilitate advancement of said sleeve into an opening defined in a wall of a body cavity, and (2) a second orientation in which the sealing members are positioned to prevent fluid communication between an area inside of the body cavity and an area outside of the body cavity through a space defined between the opening in the wall of the body cavity and the sleeve. The apparatus further includes an actuator for moving the sealing members between the first orientation and the second orientation.

Pursuant to still another embodiment of the present invention, there is provided a medical procedure. The medical procedure includes the steps of creating an opening in a wall of a body cavity, and advancing a medical apparatus through the opening and into the body cavity, the medical apparatus including (1) a sleeve having a number of sealing members, and a passageway extending therethrough, and (2) a trocar assembly positioned within the passageway of the sleeve, the trocar assembly including a cannula and a trocar. The medical procedure further includes the step of positioning the sealing members to contact an interior surface of the body cavity.

It is therefore an object of the present invention to provide a new and useful medical apparatus.

It is another object of the present invention to provide an improved medical apparatus.

It is still another object of the present invention to provide a new and useful medical apparatus for protecting a port site wound from tumor cell implantation or contamination with an infectious agent.

It is another object of the present invention to provide an improved medical apparatus for protecting a port site wound from tumor cell implantation or contamination with an infectious agent.

It is moreover an object of the present invention to provide a new and useful medical procedure for performing minimally invasive surgery.

It is still another object of the present invention to provide an improved medical procedure for performing minimally invasive surgery.

It is also an object of the present invention to provide a medical apparatus for protecting a port site wound which can be retrofit to existing trocar assembly technology.

It is still another object of the present invention to provide a medical apparatus for protecting a port site wound which adds only a minimal amount of bulk to the diameter of a trocar assembly.

The above and other objects, features, and advantages of the present invention will become apparent from the following description and attached drawings.

DETAILED DESCRIPTION OF THE PREFERRED EMBODIMENT

Figure 1:
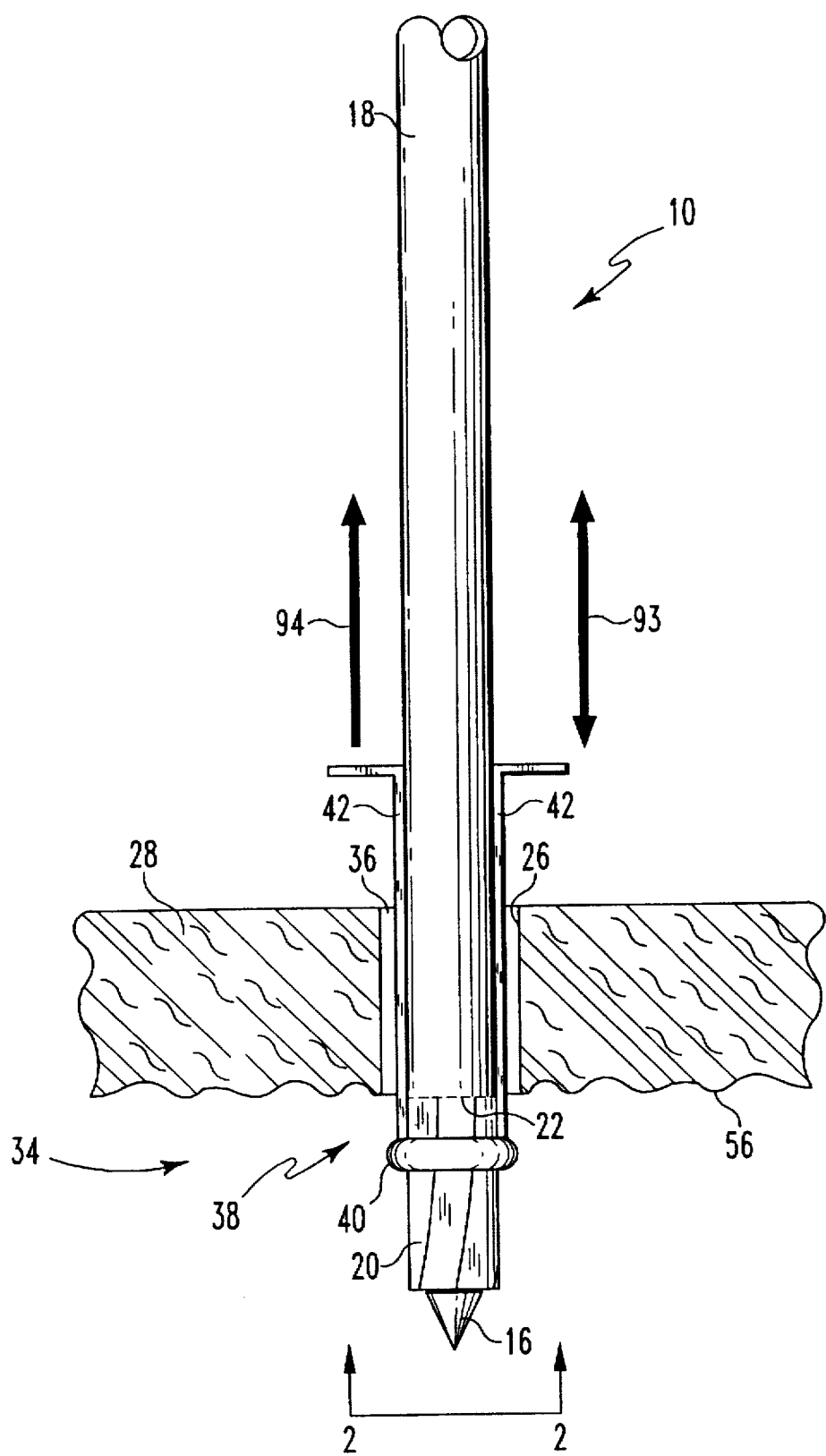
FIG. 1 is a fragmentary side elevational view of a medical apparatus inserted through a body cavity wall which incorporates the features of the present invention therein, with the body cavity wall shown in cross-section for clarity of description.

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

Figure 4:
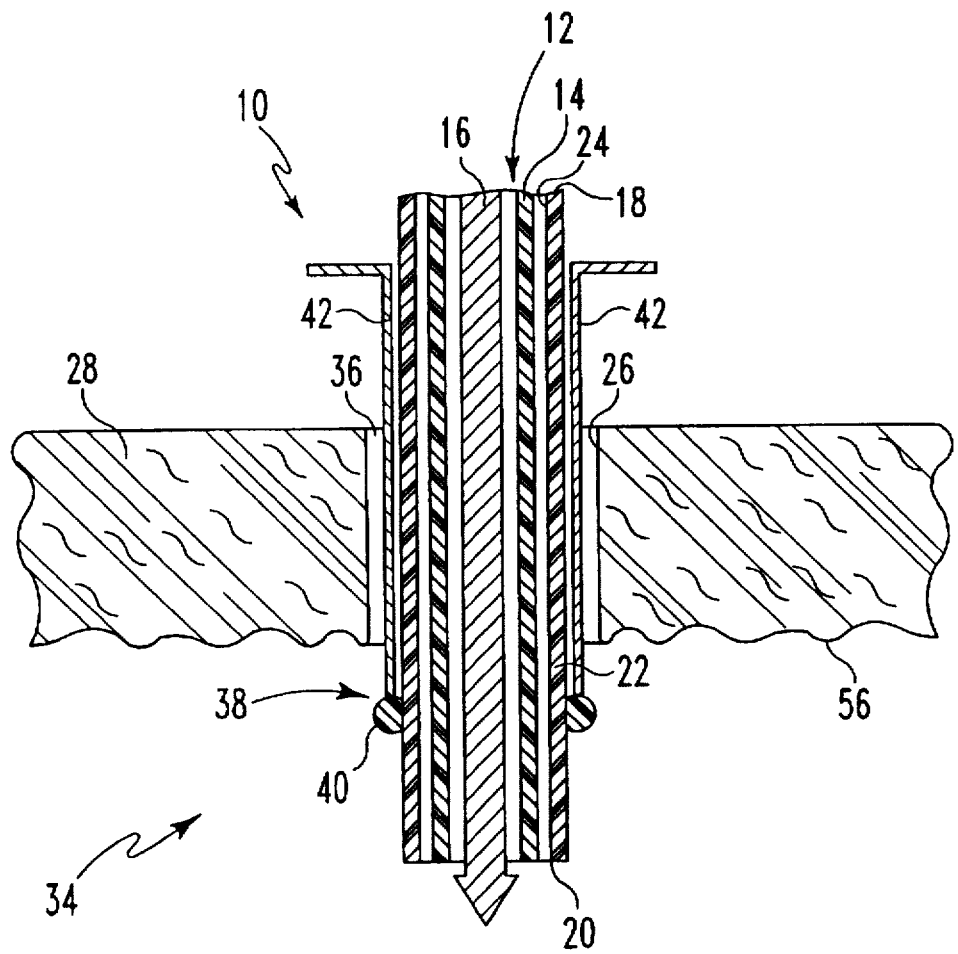
FIG. 4. is an enlarged cross sectional view of the medical apparatus of FIG. 1, with the guide member shown in a first position and the sealing members shown in a first orientation.
Figure 5:
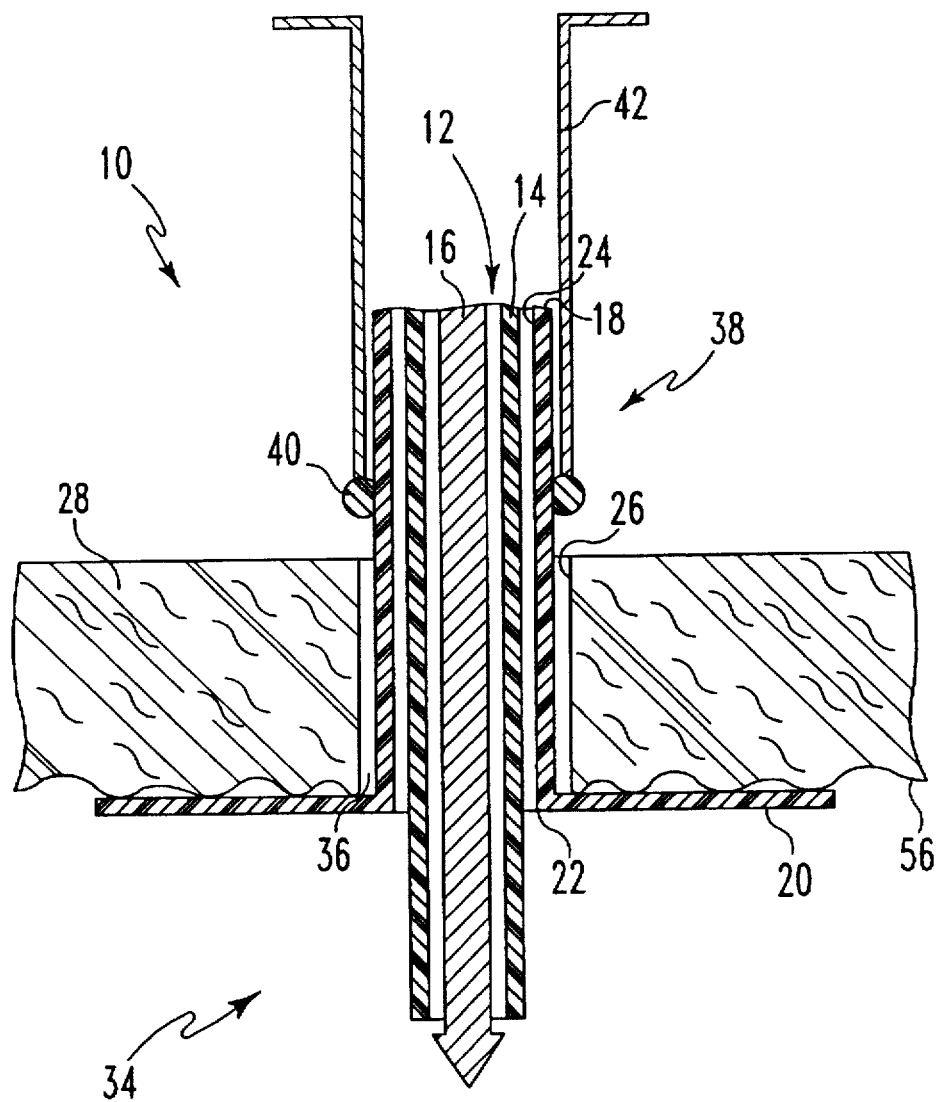
FIG. 5 is an enlarged cross sectional view of the medical apparatus of FIG. 1, with the guide member shown in a second position and the sealing members shown in a second orientation.

Referring to FIGS. 1, 4 and 5 there is shown a medical apparatus 10 of the present invention advanced through an opening 26 in a wall 28 of a body cavity 34. The medical apparatus 10 includes a sleeve 18 having a passageway 24 extending therethrough. The sleeve 18 includes a number of sealing members 20. The medical apparatus further includes an actuator 38 and a trocar assembly 12. The actuator 38 includes a guide member 40 and handles 42. The sealing members 20 extend from a distal end 22 of sleeve 18. The trocar assembly 12 includes a cannula 14 and a trocar 16 positioned within passageway 24 of the sleeve 18.

Figure 2:
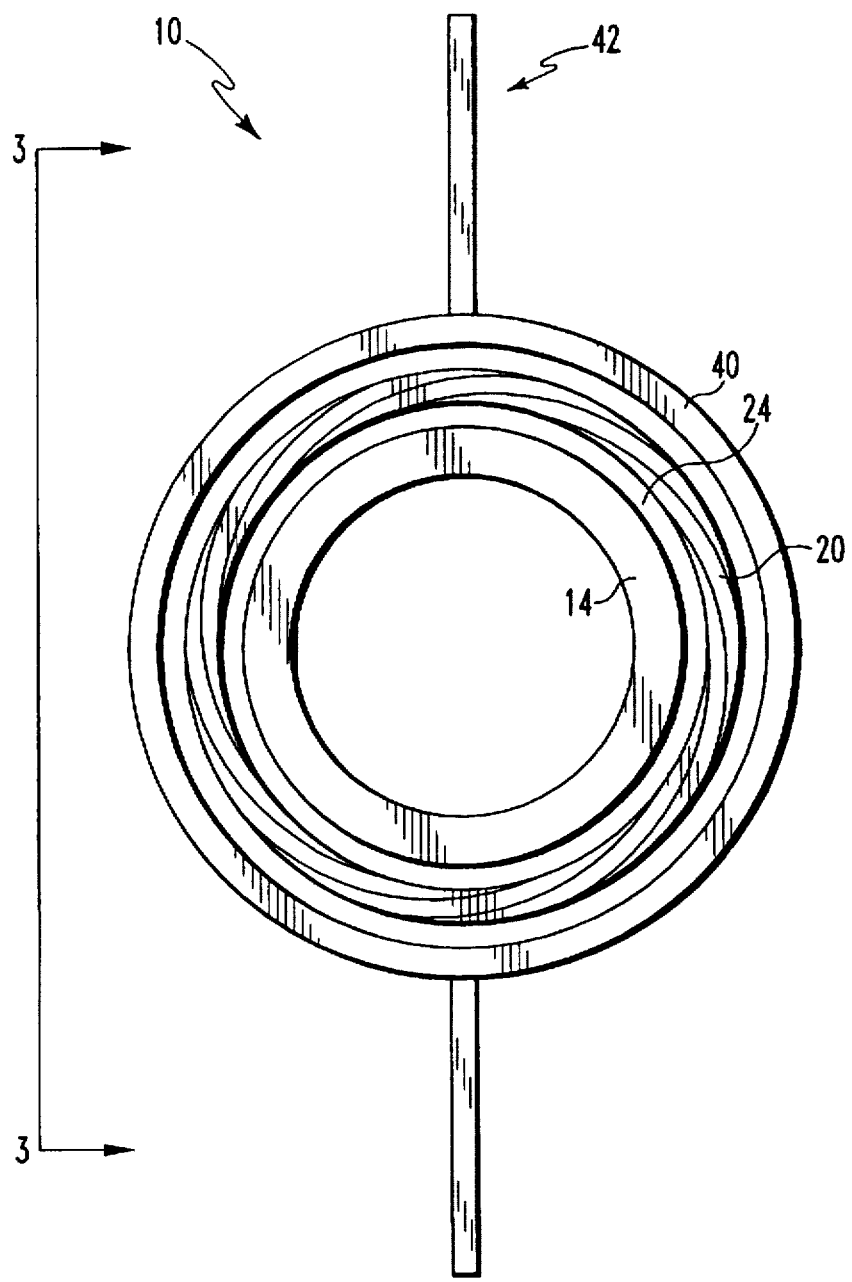
FIG. 2 is an enlarged end elevational view of the medical apparatus taken along line 2—2 of FIG. 1, with the trocar and body cavity wall shown removed for clarity of description.
Figure 3:
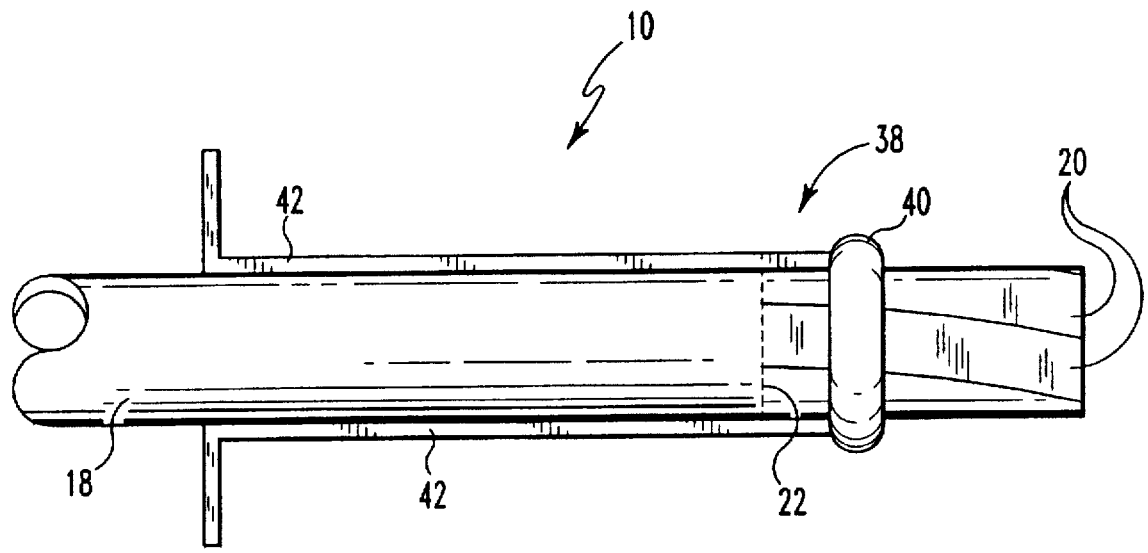
FIG. 3. is a reduced fragmentary side elevational view of the medical apparatus taken along line 3—3 of FIG. 2.

As illustrated in FIG. 2, cannula 14, sealing members 20, and guide member 40 are all respectively nested within each other in a substantially concentric relationship (a portion of handles 42 is also shown extending above guide member 40). Cannula 14 is slidably fit into passageway 24 of sleeve 18 so as to allow its movement relative to sleeve 18. It should also be understood that cannula 14 and sleeve 18 are fit in such a way as to form a substantially gas tight junction so that substantially no gas leakage occurs through this junction during insufflation of the body cavity 34. The aforementioned gas tight junction may be formed using rubber gaskets or o-rings.

Figure 6:
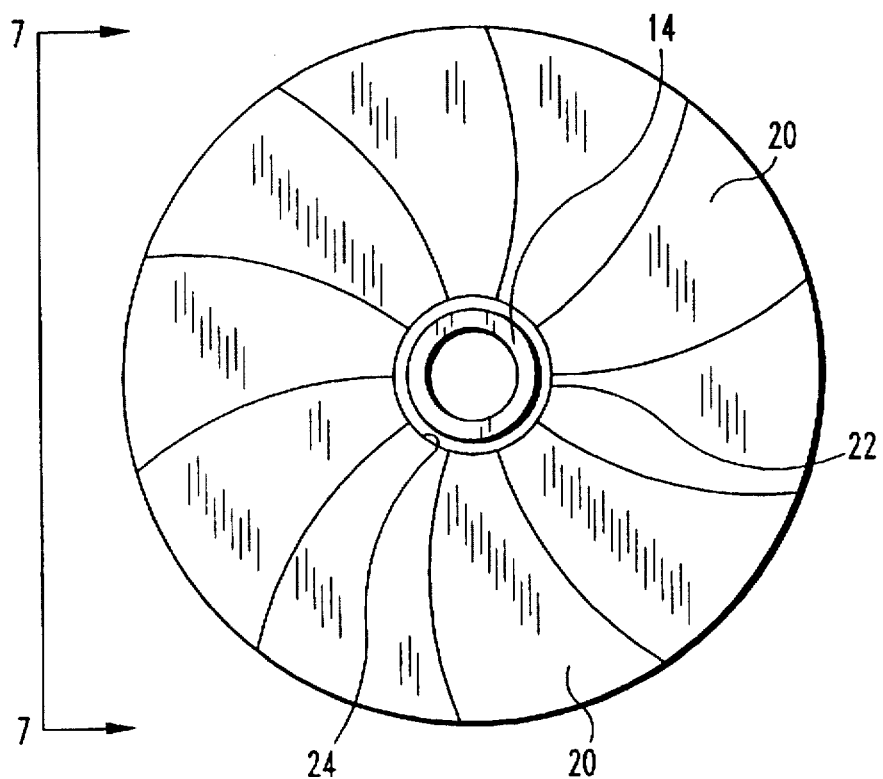
FIG. 6 is a view similar to FIG. 2, however the medical apparatus is shown reduced, and the sealing members are shown in the second orientation.
Figure 7:
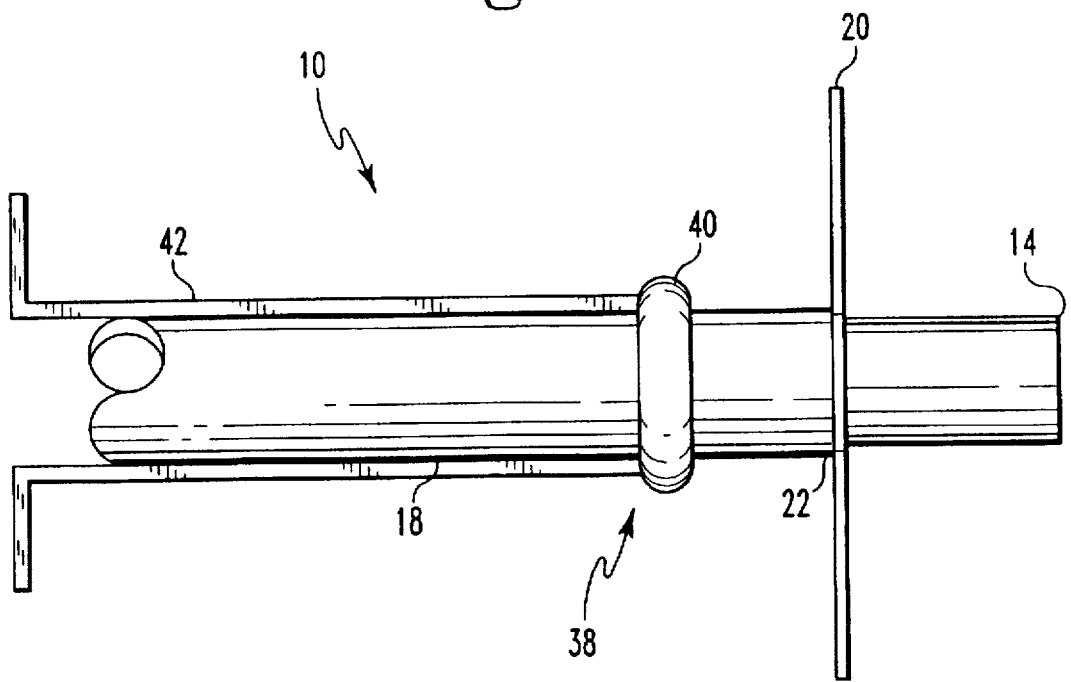
FIG. 7 is a fragmentary side elevational view of the medical apparatus taken along line 7—7 of FIG. 6.

Guide member 40 is slidably mounted onto sleeve 18 so it can be moved between a first position as shown in FIG. 4 and a second position as shown in FIG. 5. The double headed arrow 93 of FIG. 1 shows the direction of movement of guide member 40. Specifically, FIGS. 1–4 show guide member 40 placed in the first position, whereas FIGS. 5 and 7 show guide member 40 placed in the second position. As illustrated in FIGS. 1, 3, 5 and 7, the position of guide member 40 controls the movement of sealing members 20 between a first orientation and a second orientation. The sealing members 20 are positioned in the first orientation when the sealing members 20 are positioned in a substantially parallel relationship with passageway 24 of sleeve 18, as shown in FIGS. 1–4. The sealing members 20 are positioned in the second orientation when the sealing members 20 are positioned in a substantially orthogonal relationship with passageway 24 of sleeve 18 as shown in FIGS. 5–7. Moreover, as depicted in FIG. 6, when sealing members 20 are in the second orientation they extend from the distal end 22 of sleeve 18 (not shown in FIG. 6) so as to overlap one another, thereby completely surrounding passageway 24 of sleeve 18.

FIG. 6 shows sealing members 20 extending to form an annular flange. However, it should be appreciated that the present invention is not limited to the geometric shape formed by the extending sealing members. For example, other geometric shapes are contemplated, such as square or oval shaped configurations. Moreover, a single sealing member extending from a distal end of a sleeve, or a number of non-overlapping sealing members spaced around a distal end of a sleeve are also contemplated. Furthermore, sealing members having perforations thereon which can be torn and separated prior to positioning in contact with the interior surface of a body cavity wall are also contemplated.

Sleeve 18 and guide member 40 can be made from any plastic material which is conventionally used in the medical device arts. Such material would be compatible with insertion into a body cavity. It should also be noted that the guide member used in the present invention can be manufactured to a size which only adds a minimal amount of bulk to the diameter of a trocar assembly. By doing so, trauma to the body cavity wall upon insertion of the medical apparatus of the present invention will be reduced.

Sleeve 18 and sealing members 20 are formed such that when no force is applied to sealing members 20 they spontaneously assume their second orientation (see FIGS. 5-7). Moreover, sealing members 20 are flexibly attached to distal end 22 such that when force is applied (i.e. the force applied by sliding guide member 40 over the sealing members 20) the sealing members 20 assume their first orientation (see FIGS. 1-4).

Handles 42 can be made of any material having the appropriate beam strength to move guide member 40 from the first position to the second position.

When performing a medical procedure with medical apparatus 10, such as a laparoscopic surgery, guide member 40 is placed into the first position (see FIGS. 1-4) so that sealing members are maintained in their first orientation (see FIGS. 1-4). Trocar 16 of medical apparatus 10 then contacts with and is advanced through wall 28 of a body cavity 34 to create an opening 26. Preferably, sleeve 18 and trocar 16 are simultaneously advanced through the opening 26 and into body cavity 34. It should be appreciated that maintaining sealing members 20 in their first orientation facilitates the advancement of sleeve 18 through opening 26 and into body cavity 34.

Once distal end 22 of medical apparatus 10 enters into body cavity 34 through opening 26, handles 42 are moved away from opening 26 in the direction of arrow 94 (see FIG. 1) so as to slide guide member 40 to the second position (see FIGS. 5 and 7), thereby allowing sealing members 20 to assume their second orientation. Once sealing members 20 have assumed their second orientation they are positioned to contact the interior surface 56 of the body cavity wall 28 so as to prevent fluid communication between an area inside of the body cavity and an area outside of the body cavity through the space 36 defined between the opening 26 and the sleeve 18.

It should be understood that a ridge (not shown) or a number of "flange teeth" (not shown) extending from the surface of the sealing members and contacting the interior surface of the body cavity wall is also contemplated. Such a ridge or "flange teeth" will also contact the interior surface of the body cavity wall and assist in preventing fluid communication between the area inside of the body cavity and the area outside of the body cavity through the space defined between the opening and the sleeve. The aforementioned ridge or "flange teeth" will also keep the sealing members stationary relative to the interior surface of the body cavity during manipulations of the cannula.

Once the medical procedure is completed, handles 42 are moved toward opening 26 in a direction opposite to arrow 94 so as to slide guide member 40 to the first position (see FIGS. 1-4). The movement of guide member 40 to the first position forces sealing members 20 to assume their first orientation (see FIGS. 1-4), thereby facilitating the removal of medical apparatus 10 from opening 26.

Figure 8:
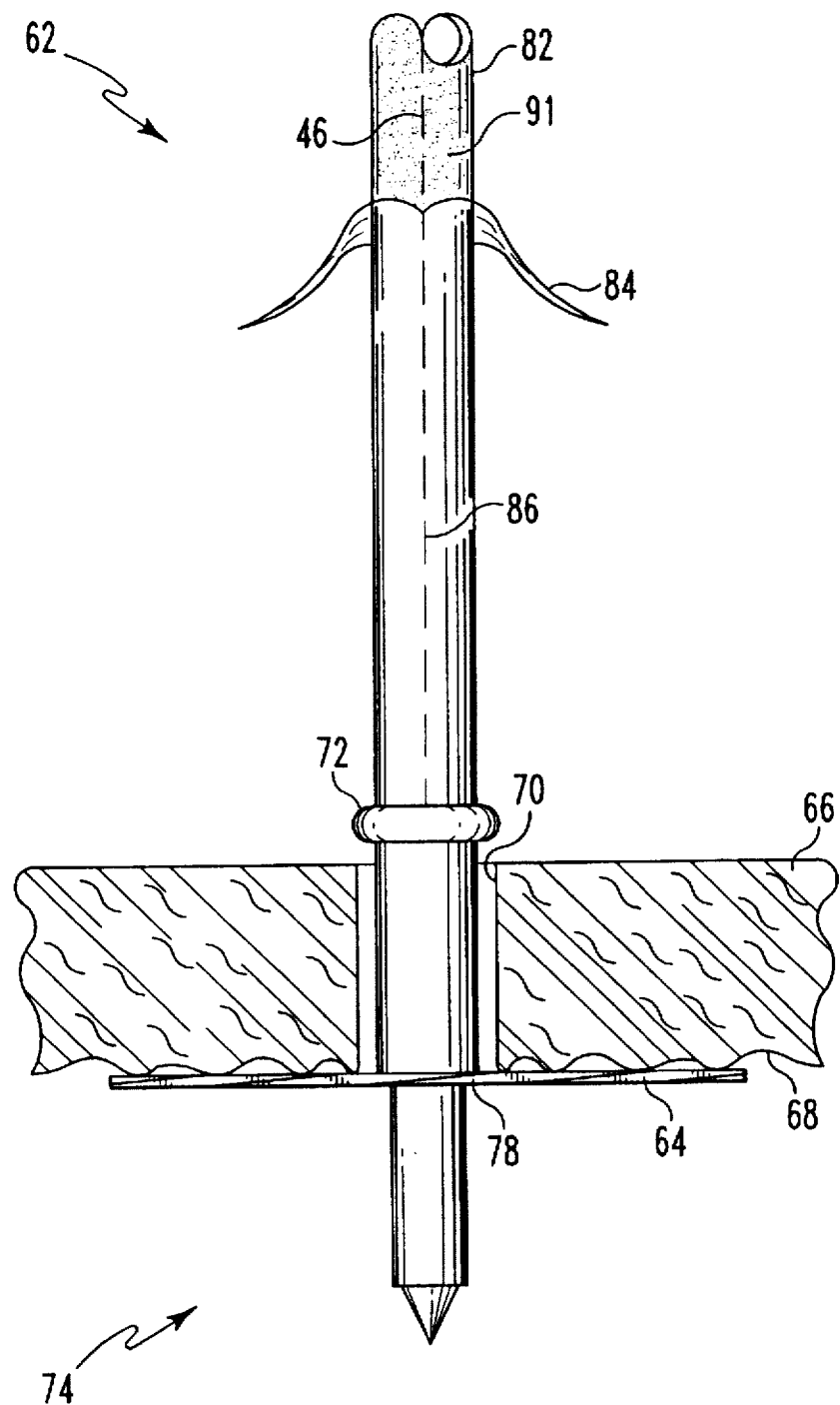
FIG. 8 is a fragmentary side elevational view of a medical apparatus similar to the one shown in FIG. 1, but this medical apparatus includes a strippable liner thereon (the handles are shown removed for clarity of description)

Now referring to FIG. 8, there is shown a medical apparatus 62 similar to the medical apparatus 10 shown in FIG. 1. Medical apparatus 62 is shown advanced through an opening 70 in a wall 66 of a body cavity 74. The medical apparatus 62 includes a sleeve 82 having a plurality of perforations 46 defined in its proximal end portion and an adhesive material disposed on its outer surface 91. The sleeve 82 includes a number of sealing members 64 positioned in a second orientation extending from distal end 78. The medical apparatus 62 further includes a guide member 72 positioned in the second position. Medical apparatus 62 also includes a strippable line 84, surrounding and in contact with, the adhesive material disposed on outer surface 91. The strippable liner has perforations 86 formed thereon.

Figure 9:
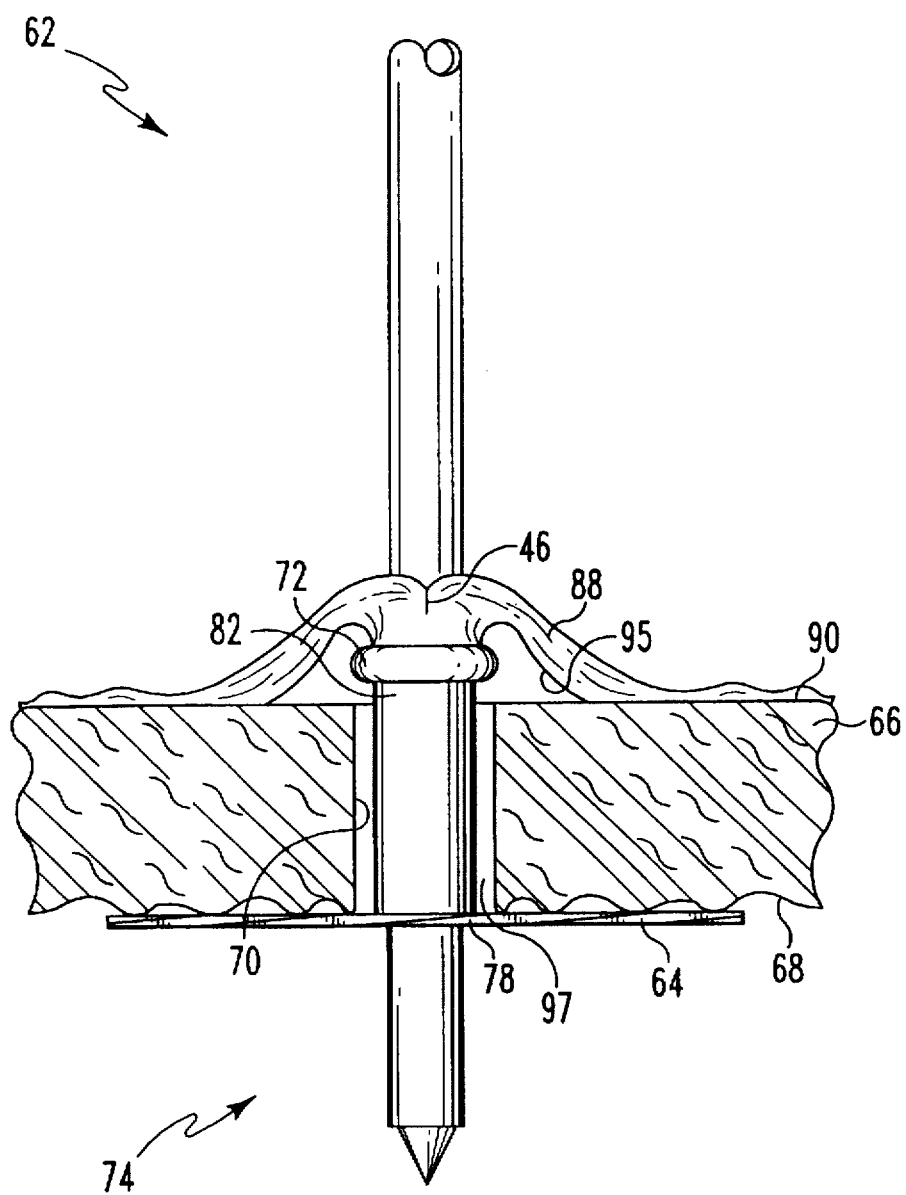
FIG. 9 is a fragmentary side elevational view of the medical apparatus shown in FIG. 8, with the strippable liner peeled off, and the sleeve peeled down and attached to an exterior surface of a body cavity wall.

Medical apparatus 62 is used in the same manner as described above with reference to medical device 10. However, once the sealing members are positioned in contact with an interior surface 68 of body cavity wall 66, strippable liner 84 is torn along perforations 86 to expose the adhesive material disposed on the outer surface 91 of sleeve 82. As shown in FIG. 9, sleeve 82 is then torn along perforations 46 down to guide member 72 to form a number of elongated strips 88 having a first surface 95 with the adhesive disposed thereon. It is also contemplated that sleeve 82 may be formed from a material having the physical property of molecular orientation whereby a tear in the material runs readily only in a longitudinal direction along the length of sleeve 82. A sleeve formed from such a material will eliminate the need for the above described perforations. Once the elongated strips 88 are formed, a first surface 95 of each strip 88 is attached to an exterior surface 90 of body cavity wall 66 with the adhesive.

An important aspect of using elongated strips 88 in the above described manner is that they cooperate with sealing members 64 to stabilize the position of medical apparatus 62 in opening 70. The attachment of elongated strips 88 to the exterior surface 90 of body cavity wall 66 also keeps sealing members 64 in contact with interior surface 68. This ensures that no fluid communication exists between an area inside of the body cavity 74 and an area outside the body cavity through the space 97 defined between the opening 70 and the sleeve 82.

Based upon the above description it will be understood by those skilled in the art that the present invention provides a medical apparatus for protecting a port site wound which adds only a minimal amount of bulk to the diameter of a trocar assembly. Moreover, it will be understood by those skilled in the art that the medical apparatus of the present invention can be retrofit to existing trocar assembly technology. Furthermore, the medical apparatus of the present invention allows minimally invasive surgical techniques, such as laparoscopic surgery, to be safely applied to cancer surgery.

While the invention has been illustrated and described in detail in the drawings and foregoing description, such illustration and description is to be considered as exemplary and not restrictive in character, it being understood that only the preferred embodiments have been shown and described and that all changes and modifications that come within the spirit of the invention are desired to be protected. For example, while the mechanism described above for moving the sealing members from the first orientation to the second orientation has many benefits, other mechanisms may be used. One such mechanism may utilize pressure in the body cavity to force the sealing members against the interior surface thereof.

What is claimed is:

1. A medical apparatus, comprising:
   a trocar assembly including a cannula and a trocar, wherein (1) said cannula has a lumen defined therein, and (2) said trocar is completely removable from said lumen of said cannula;
   a sleeve having a number of sealing members extending therefrom and a passageway extending therethrough, said trocar assembly being positioned within said passageway of said sleeve, wherein said sleeve is positionable within an opening defined in a wall of a body cavity, and wherein said sealing members are movable between (1) a first orientation in which said sealing members are positioned to facilitate advancement of said sleeve into the opening, and (2) a second orientation in which said sealing members are positioned to prevent fluid communication between an area inside of the body cavity and an area outside of the body cavity through a space defined between the opening of the body cavity and said sleeve, wherein said sealing members partially overlap one another when said sealing members are positioned in the second orientation whereby fluid leakage between adjacent sealing members is prevented.

2. A medical apparatus, comprising:

a trocar assembly including a cannula and a trocar, wherein (1) said cannula has a lumen defined therein, and (2) said trocar is completely removable from said lumen of said cannula; and a sleeve having a number of sealing members extending therefrom and a passageway extending therethrough, said trocar assembly being positioned within said passageway of said sleeve, wherein said sleeve has a plurality of perforations defined in a proximal end portion thereof whereby tearing of said proximal end portion is facilitated.

3. The medical apparatus of claim 2, wherein said proximal end portion has an adhesive material disposed thereon.

4. A medical apparatus, comprising:

a sleeve having a number of sealing members connected thereto and a passageway extending therethrough, said sealing members being movable between (1) a first orientation in which said sealing members are positioned to facilitate advancement of said sleeve into an opening defined in a wall of a body cavity and (2) a second orientation in which said sealing members are positioned to prevent fluid communication between an area inside of the body cavity and an area outside of the body cavity through a space defined between the opening in the wall of the body cavity and said sleeve;

an actuator for moving said sealing members between the first orientation and the second orientation; and a trocar assembly positionable within said passageway of said sleeve, said trocar assembly including a cannula and a trocar, wherein (1) said cannula has a lumen defined therein, and (2) said trocar is completely removable from said lumen of said cannula, wherein said sealing members partially overlap one another when said sealing members are positioned in the second orientation whereby fluid leakage between adjacent sealing members is prevented.

5. A medical apparatus, comprising:

a sleeve having a number of sealing members connected thereto and a passageway extending therethrough, said sealing members being movable between (1) a first orientation in which said sealing members are positioned to facilitate advancement of said sleeve into an opening defined in a wall of a body cavity, and (2) a second orientation in which said sealing members are positioned to prevent fluid communication between an area inside of the body cavity and an area outside of the body cavity through a space defined between the opening in the wall of the body cavity and said sleeve;

an actuator for moving said sealing members between the first orientation and the second orientation; and a trocar assembly positionable within said passageway of said sleeve, said trocar assembly including a cannula and a trocar, wherein (1) said cannula has a lumen defined therein, and (2) said trocar is completely removable from said lumen of said cannula, wherein said sleeve has a plurality of perforations defined in a proximal end portion thereof whereby tearing of said proximal end portion is facilitated.

6. The apparatus of claim 5, wherein said proximal end portion has an adhesive material disposed thereon.

7. A medical procedure, comprising the steps of:

creating an opening in a wall of a body cavity;

advancing a medical apparatus through the opening and into the body cavity, said medical apparatus including (1) a sleeve having a number of sealing members connected thereto and a passageway extending therethrough, and (2) a trocar assembly positioned within the passageway of said sleeve, said trocar assembly including a cannula and a trocar, wherein (a) said cannula has a lumen defined therein, and (b) said trocar is completely removable from said lumen of said cannula; and positioning said sealing members to contact an interior surface of said body cavity, wherein said sleeve has a plurality of perforations defined in a proximal end portion thereof, and further comprising the steps of:

tearing said sleeve along the perforations so as to form a number of elongated strips; and attaching the elongated strips to an exterior surface of the wall of the body cavity.

8. The medical procedure of claim 7, wherein:

said proximal end portion has an adhesive material disposed thereon, and said attaching step includes the step of attaching the elongated strips to an exterior surface of the wall of the body cavity with said adhesive material.

* * * * *